United States Patent
Kipshidze et al.

(10) Patent No.: US 9,572,700 B1
(45) Date of Patent: Feb. 21, 2017

(54) PERCUTANEOUS ENDOVASULAR TREATMENT FOR OBESITY BY SELECTIVELY DELIVERING PARTICLES INTO THE DISTAL PORTION OF THE LEFT GASTRIC ARTERY

(71) Applicant: ENDOBAR SOLUTIONS LLC, Orangeburg, NY (US)

(72) Inventors: Nickolas Kipshidze, New York, NY (US); Martin B. Leon, New York, NY (US)

(73) Assignee: Endobar Solutions LLC, Orangeburg, NY (US)

( * ) Notice: Subject to any disclaimer, the term of this patent is extended or adjusted under 35 U.S.C. 154(b) by 98 days.

(21) Appl. No.: 14/091,787

(22) Filed: Nov. 27, 2013

Related U.S. Application Data

(60) Provisional application No. 61/775,070, filed on Mar. 8, 2013.

(51) Int. Cl.
  *A61F 5/00* (2006.01)
  *A61L 31/14* (2006.01)
(52) U.S. Cl.
  CPC .......... *A61F 5/0076* (2013.01); *A61F 5/0089* (2013.01); *A61L 31/14* (2013.01)
(58) Field of Classification Search
  CPC ........ A61B 17/12109; A61B 17/12104; A61B 17/12145; A61F 5/0076
  USPC .................. 604/507, 508, 523, 909
  See application file for complete search history.

(56) References Cited

U.S. PATENT DOCUMENTS

| 7,402,320 | B2 | 7/2008 | Mirizzi et al. |
| 2005/0015073 | A1* | 1/2005 | Kataishi et al. ............. 604/528 |
| 2006/0251582 | A1* | 11/2006 | Reb .............................. 424/9.41 |
| 2011/0065660 | A1* | 3/2011 | Baron et al. .................... 514/26 |
| 2011/0182998 | A1* | 7/2011 | Reb et al. ..................... 424/499 |
| 2013/0096580 | A1 | 4/2013 | Cohn et al. |

OTHER PUBLICATIONS

Bawudun D, Xing Y, Liu WY, Huang YJ, Ren WX, Ma M, Xu XD, Teng GJ, Ghrelin suppression and fat loss after left gastric artery embolization in canine model, Feb. 25, 2012, Cardiovasc Intervent Radiol.*

Casteel, B., Embolization procedure lowers levels of 'hunger hormone,' leads to weight loss, American College of Cardiology, Mar. 8, 2013.

(Continued)

*Primary Examiner* — Imani Hayman
*Assistant Examiner* — Hamza Darb
(74) *Attorney, Agent, or Firm* — Potomac Law Group, PLLC

(57) ABSTRACT

Weight loss can be promoted by introducing a microcatheter into the mid segment or distal portion of a human subject's left gastric artery and delivering, via the microcatheter, a plurality of particles with sizes between 300 and 500 μm into the distal portion of the subject's left gastric artery. The particles cause endovascular flow reduction or interruption in the distal portion of the subject's left gastric artery. The reduced or interrupted blood flow decreases the production of the hormone ghrelin, which reduces the subject's appetite, thereby promoting weight loss.

14 Claims, 3 Drawing Sheets

(56) References Cited

OTHER PUBLICATIONS

Arepally et al., Catheter-directed Gastric Artery Chemical Embolization for Modulation of Systemic Ghrelin Levels in a Porcine Model, Radiology, Jul. 2007, vol. 244 No. 1, pp. 138-143.
Arepally et al., Catheter-directed Gastric Artery Chemical Embolization Suppresses Systemic Ghrelin Levels in a Porcine Model, Radiology, Oct. 2008, vol. 249 No. 1, pp. 127-133.
Bawudun D. et al., Ghrelin Suppression and fat loss after left gastric artery embolization in canine model, Cardiovasc Intervent Radiol, Feb. 2012.
Cortez, Sealing the Artery with Hunger Hormone Cuts Pounds, Bloomberg, Mar. 7, 2013.
Bowdler, Electronic implant designed to reduce obesity to undergo trials, BBC News, Mar. 28, 2013.
Cummings, D, Grelin and Gastric Bypass: Is There a Hormonal Contribution to Surgical Weight Loss?, Journal of Clinical Endocrinology & Metabolism vol. 88, pp. 2999-3002 (2003).
Guimaraes, et al., Does Material Matter? Particulate Embolics, Endovascular Today, Apr. 2013, pp. 70-74.
Harsch et al., Leptin and ghrelin levels in patients with obstructive sleep apnoea; effect of CPAP treatment, European Respiratory Journals, 2003.
Reinberg, Procedure Lowers 'Hunger Hormone' to Help Obese Lose Weight. US News and World Report, Mar. 8, 2013.
ACC: Gastric Artery Embolization Viable in Humans, Physician's Briefing, Health News Articles, 2013.
Terumo Heatrail II-Guiding Catheter, Nov. 6, 2013 HD.
Kipshidze, N., Endovascular Treatment of Obesity: Results from First in Man Study, Innovations in Cardiovascular Interventions Meeting, Dec. 2-4, 2012.
Kipshidze, N., Endevascular Treatment of Obesity: Early Results from First in Man Study, JACC: Cardiovascular Interventions, vol. 6, No. 2, Suppl. S, Feb. 23-26, 2013.
Kipshidze, N., First-in-Man Study of Left Gastric Artery Embolization for Weight Loss, JACC: Abstracts of Original Contributions, vol. 61, No. 10, Suppl. A, Mar. 12, 2013.
Morris, D., Embolization of the left gastric artery in the absence of angiographic extravasation, Cardio Vascular and Interventional Radiology, 1986, vol. 9, Issue 4, pp. 195-198.
Gastric artery embolization suppresses 'hunger hormone,' leads to weight loss, Yahoo Lifestyle India, Mar. 8, 2013.
Bawudun D. et al., Ghrelin Suppression and fat loss after left gastric artery embolization in canine model, Cardiovasc Intervent Radiol, Feb. 2012—7 pages, Full Version.

* cited by examiner

PERCUTANEOUS ENDOVASCULAR TREATMENT FOR OBESITY BY SELECTIVELY DELIVERING PARTICLES INTO THE DISTAL PORTION OF THE LEFT GASTRIC ARTERY

CROSS REFERENCE TO RELATED APPLICATIONS

This Application claims the benefit of U.S. Provisional Application 61/775,070, filed Mar. 8, 2013, which is incorporated herein by reference.

BACKGROUND

Obesity is widely recognized as a major public health issue resulting in decrease of quality of life and development of chronic diseases, such as metabolic syndrome, diabetes, hypertension, congestive heart failure, atherosclerosis, sleep apnea, etc. Lifestyle changes can be used to treat obesity, but lifestyle changes are not always achievable, especially in long term prospect. Drug therapy is one conventional treatment for obesity, but it is often accompanied by various complications and adverse side effects.

Bariatric surgery is another conventional treatment for obesity. One of the recognized benefits of bariatric surgery is the decreased production of ghrelin. Ghrelin, a neuropeptide which is predominantly produced in the gastric fundus, is the only known hormone that stimulates food intake (orexigenic hormone). It is believed that the decreased production of ghrelin that is associated with bariatric surgery helps promote weight loss. But bariatric surgery is invasive and can be accompanied by considerable surgical complications and/or adverse side effects.

SUMMARY OF THE INVENTION

One aspect of the invention relates to a method of promoting weight loss. This method includes the steps of introducing a microcatheter into the mid segment or distal portion of a human subject's left gastric artery, and delivering, via the microcatheter, a plurality of particles with sizes between 300 and 500 μm into the distal portion of the subject's left gastric artery, so that the particles cause endovascular flow reduction or interruption in the distal portion of the subject's left gastric artery.

In some embodiments, the step of introducing the microcatheter into the mid segment or distal portion of the subject's left gastric artery includes the steps of introducing a guiding catheter into the subject's left gastric artery, and guiding the microcatheter through the guiding catheter and into the mid segment or distal portion of the subject's left gastric artery.

DETAILED DESCRIPTION OF THE PREFERRED EMBODIMENTS

Figure 1:
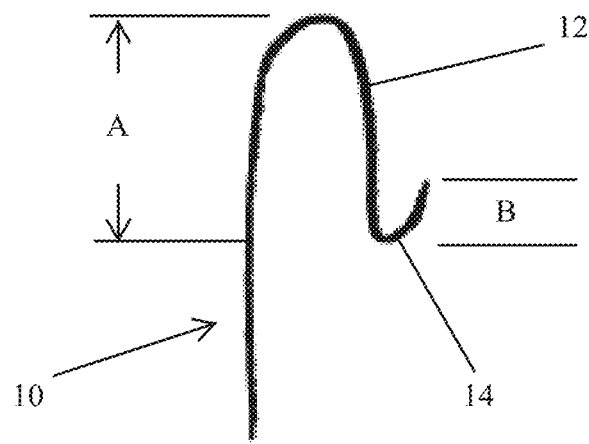
FIG. 1 depicts an example of a suitable shape for the distal end of a custom-shaped guiding catheter with an S-shaped bend.

Percutaneous endovascular modification of the function of the gastric fundus using particulate embolization of the distal portion of the left gastric artery is less invasive and more cost effective alternative to bariatric surgery for achieving weight loss.

This application describes a novel approach which involves modifying the arterial blood flow to the gastric fundus by means of percutaneous endovascular flow reduction (or interruption) in the distal portion of the left gastric artery. Experiments in humans (performed outside the U.S.) has demonstrated dramatic weight loss at one month after procedure and sustained for six months follow-up with no reported adverse effects. While reduction in the hunger-mediating peptide hormone ghrelin (secreted in the gastric fundus) has been identified as a one of possible mechanism, the complete physiologic mechanism is not yet clear and may well involve other hormones and/or changes in gastric motility with consequent reduction in hunger sensation in experimental subjects.

The approach described herein achieves endovascular flow reduction or interruption by introducing a plurality of particles into the distal portion of the subject's left gastric artery. The particles, also referred to herein as microparticles, preferably have sizes between 300 and 500 μm, and are delivered via a microcatheter. The particles are preferably compressible and spherical. They are preferably made of polyvinyl alcohol, and more preferably made of acrylamido polyvinyl alcohol. One suitable commercially available product for this purpose is BeadBlock Embolic Beads, 300-500 μm compressible microspheres (Biocompatibles UK Limited, Surrey, UK).

Alternative commercially available products for this purpose include polyvinyl alcohol (PVA foam embolization particles, Cook Medical, Bloomington, Ind.); hydrogel core with Polyzene-F coating (Embozene™ microspheres, CeloNova Biosciences, Inc., San Antonio, Tex.); microspheres made from trisacryl cross linked with gelatin (Embosphere microspheres, Merit Medical Systems, Inc., South Jordan, Utah); HepaSphere™ Microspheres, which are made from two monomers (vinyl acetate and methyl acrylate) that combine to form a copolymer (sodium acrylate alcohol copolymer); Bearing™ nsPVA Embolization Particles, which are irregularly-shaped, biocompatible, hydrophilic, nonresorbable particles produced from polyvinyl alcohol; EmboGold™ Microspheres, which are made from trisacryl cross linked with gelatin and impregnated with 2% elemental gold for visibility; QuadraSphere™ Microspheres, which are also made from two monomers (vinyl acetate and methyl acrylate) that combine to form a copolymer (sodium acrylate alcohol copolymer), and Terumo Bead BlockT microspheres. In alternative embodiments, other embolization materials may be used, including but not limited to coils, other microparticles, foams, different synthetic or organic gels, thrombin, fibrin, collagen, fibrinogen (liquid or powder), and any other material that can occlude blood vessel.

Optionally, certain substances may be added to the particles (or to the other embolization materials) to enhance the effect of the procedure. Examples include, but are not limited to: pharmaceuticals, genetic materials, or different types of cells that also help to decrease production of ghrelin and/or other hormones or other substances that effect appetite in humans.

The procedure involves inserting a catheter into the left gastric artery, which is the major vessel that supplies gastric fundus and modify blood flow. FIG. 8 depicts one way to accomplish this, which is to insert a guiding catheter via the femoral artery or radial artery until the left gastric artery is engaged (in other words, until the distal end of the guiding catheter is introduced into the subject's left gastric artery) (step S2). Although the inventor is not aware of any guiding catheters that are specially designed to engage the left gastric artery, examples of suitable guiding catheters for this step include catheters that are already available for other applications such as for coronary angiography and or coronary stenting. In one preferred embodiment, the guiding catheter is a 6 French Heartrail II JR-4.0 guiding catheter (Terumo Europe N.V., Leuven, Belgium). That particular guiding catheter is a Judkins Right type catheter and has a JR-4.0 shape code. In alternative embodiments, a custom-shaped guiding catheter may be used for obtaining easy access to left gastric artery. An example of one suitable shape for such a guiding catheter is provided in FIG. 1, in which the distal end 12 of the custom-shaped guiding catheter 10 has an S-shaped bend. This shape is similar to the shape of the Surefire Axis Catheter (Surefire Medical Inc., Westminster Colo.), but the distal-most bend 14 is increased from about 45° to about 160'. Suitable dimensions for the guiding catheter 10 for accessing the left gastric artery are as follows: A between 3 and 4 inches; and B between ½ and 1 inch.

After the guiding catheter is in position, a microcatheter is then guided through the guiding catheter and introduced into the mid segment or distal portion of the subject's left gastric artery (step S4). Once the distal end of the microcatheter has been inserted into the mid segment or distal portion of left gastric artery, the embolization material is delivered into the distal portion of left gastric artery via the microcatheter (step S6), The distal shaft of the microcatheter must be small, e.g., 2 French in diameter. One example of a commercially available microcatheter that is suitable for this purpose is the Excelsior 1018 Microcatheter (Boston Scientific Corp., Corck, Ireland).

The presence of the embolization material in the distal portion of left gastric artery will reduce or interrupt the blood flow in the distal portion of left gastric artery (step S8), which will modify the blood supply to the fundus of stomach. More specifically, it reduce or interrupt the blood supply to the fundus.

Using microparticles for the embolization material in step S6 (as opposed to other types of embolization materials) is advantageous because they are inert, biocompatible, and flow-directed. Moreover, when used as described herein, they will not cause tissue necrosis or unwanted non-target embolization. In contrast, if a chemical-based embolization material such as sodium morrhuate is used instead of the preferred microparticles, deep penetration and or extravasation of this sclerotherapy agent into the gastric tissue may lead to local edema and/or extensive inflammation that results in gastric ulceration and necrosis. Chemical-based embolization material may also lead to systemic toxicity and non-target embolization that may damage the liver, spleen or other organs.

Using particles with sizes between 300 and 500 µm in step S6 is advantageous because using smaller particles (e.g., 50-100 µm) can result in mucosal necrosis of the fundus, and gastric ulcers. It can also result in non-target embolization of, for example, the esophagus, the liver, and/or the spleen because the small particles can penetrate very deep into tissue and destroy gastric mucosa. Animal experiments have shown that such smaller particles may also end up in structures other than the fundus. In addition, using larger particles (e.g., 700-1000 µm) can result in gastric ulcers, and non-target embolization of, for example, the esophagus, the liver, and/or the spleen. This may be due to deformation of the particles during injections and the formation of larger clusters, which can lead to more proximal embolization. It may also be due to reflux of the particles due to the Venturi effect. In contrast, when particles with sizes between 300 and 500 µm are used, these problems are avoided or at least minimized.

Limiting the delivery of the particles to the distal portion of the subject's left gastric artery in step S6 is advantageous because when the proximal portion of the left gastric artery is also filled with particles, the risk of esophageal and nonfundus gastric ulcers is very high. More specifically, it was observed in three out of three subjects in animal studies, when tested in pigs. In contrast, these problems were not observed in any of the three pig subjects in which the delivery of the particles was limited to the distal portion of the test subject's left gastric artery.

Thus, by using the correct size of the correct material and delivering it to the correct location, many of the problems associated with other approaches are avoided, and the procedure can be made safe.

EXAMPLE 1

A study was done on five obese subjects to determine the feasibility, safety, and efficacy of embolization of the distal portion of the left gastric artery to reduce plasma ghrelin levels and body weight.

All subjects underwent gastroscopy prior the embolization to assess for the presence of peptic ulcer or gastritis. Gastritis was found in two subjects who subsequently underwent medical treatment. Embolization was performed only after follow-up gastroscopy showed significant improvement in mucosal irritation.

Weights were measured and routine blood samples obtained including a complete blood count, electrolytes, and creatinine prior to embolization.

In the procedure, 6-Fr femoral access was obtained. More specifically, a 6-Fr Heartrail II JR-4.0 guiding catheter (Terumo Europe N.V., Leuven, Belgium) was used to engage the celiac trunk ostium and angiography performed in different projections in order to identify the origin and anatomy of left gastric artery. In some cases, a 0.35" guidewire was advanced into the common hepatic or splenic arteries to stabilize the guiding catheter position.

The left gastric artery, a branch of the celiac trunk, was wired with a 0.014" Runthrough NS PTCA Guide Wire (Terumo Europe N.V., Leuven, Belgium) and an Excelsior 1018 Microcatheter (Boston Scientific Corp., Corck, Ireland) advanced over the guide wire into the mid segment of the left gastric artery. Subsequently, the guide wire was removed while maintaining the microcatheter position in the left gastric artery and selective angiography performed to ensure proper catheter position and define the anatomy and course of the left gastric artery. Angiography of the left gastric artery and the surrounding anatomy was performed after a radio-opaque material was injected into the left gastric artery, but prior to the injection of any particles. Dark artifacts in the resulting angiogram revealed that blood was flowing in the distal portion of the left gastric artery.

Repeat injections of small amounts of BeadBlock Embolic Bead, 300-500 μm compressible microspheres (Biocompatibles UK Limited, Surrey, UK) mixed with contrast agent (1:1 ratio) were then performed. Angiography was performed between injections of the microspheres to assess left gastric artery flow characteristics. The injection of the microspheres was continued until distal portions of artery branches were no longer visible during radio-opaque contrast injection. This was observed in another angiogram, which depicted the left gastric artery and the surrounding anatomy. The absence of dark artifacts in the relevant portion of this angiogram indicated that blood was no longer flowing in the distal portion of the left gastric artery.

The guiding and microcatheter were then withdrawn and subjects transferred to a ward, where the introducer sheath was removed and manual pressure applied to obtain hemostasis.

Esophagogastroscopy was performed in all subjects before and after the procedure gastroscopy. A second follow-up gastroscopy was performed one week after the procedure. Weight and fasting plasma ghrelin levels were obtained at baseline and the 1, 3, and 6-month follow-up visits. To obtain the ghrelin levels, clotted blood samples were centrifuged to separate out blood plasma. Fasting levels of ghrelin, ALT, AST, urea and uric acid were then measured. Ghrelin was measured using the Human Ghrelin (TOTAL) RIA KIT (Merck Millipore). Subject's weight and body mass index (BMI) was also calculated at each of the visits.

Figure 2:
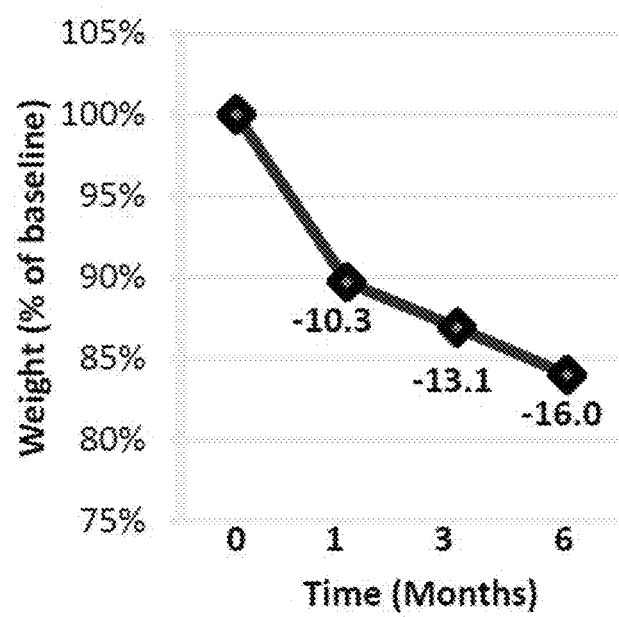
FIG. 2 is a graph that shows how the weight of the subjects changed over time.
Figure 3:
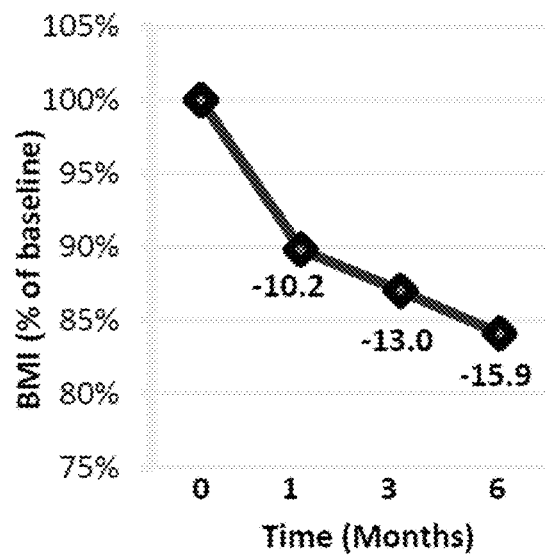
FIG. 3 is a graph that shows how the BMI (body mass index) of the subjects changed over time.
Figure 4:
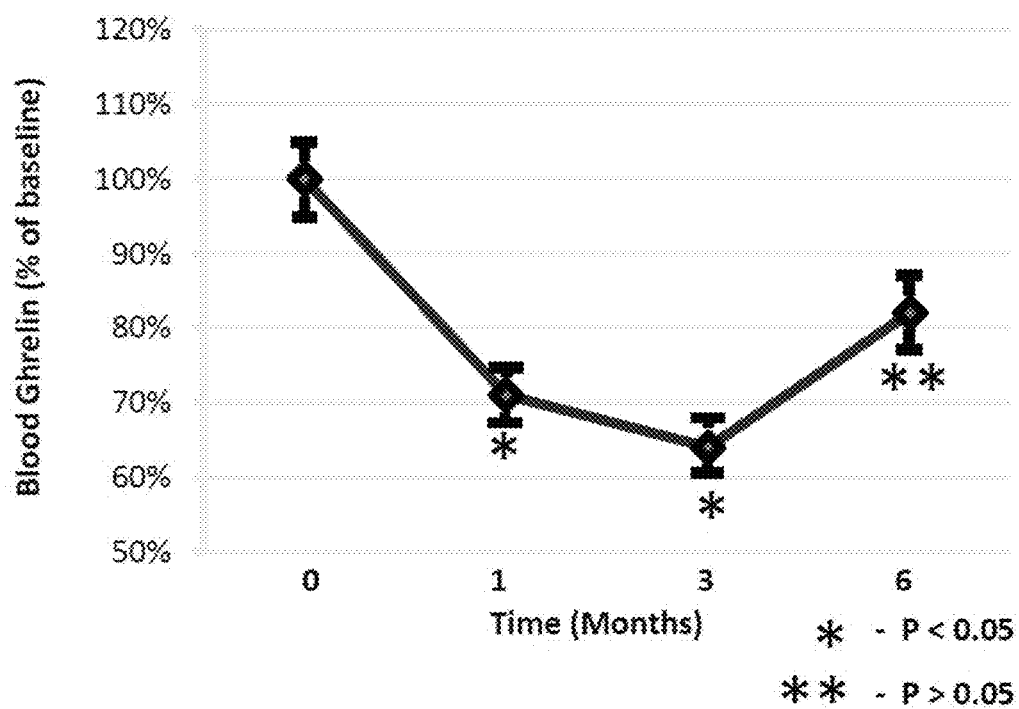
FIG. 4 is a graph that shows how the ghrelin level in the subjects' blood changed over time.

Data for the study is presented below. Table 1 shows the subject data, Table 2 shows the weight at each visit for each subject, Table 3 shows the corresponding BMI, and Table 4 shows the ghrelin levels at each visit for each subject. FIGS. 2, 3, and 4 depict the data in Tables 2, 3, and 4, respectively, in a graphical format.

TABLE 1

| Parameter | Value |
| --- | --- |
| Number of participants | 5 |
| Gender female/male (%) | 20/80% |
| Age female/male (years) | 44.7 ± 7.4 |
| Weight (kg) | 128.1 ± 24.4 |
| BMI (kg/m2) | 42.2 ± 6.8 |
| Ghrelin (pg/ml) | 473.4 ± 189.11 |

TABLE 2

| Subject # | Initial weight (kg) | Weight at 1 month FU | Weight at 3 month FU | Weight at 6 month FU |
| --- | --- | --- | --- | --- |
| 1 | 119 | 102 | 99 | 94 |
| 2 | 165 | 146 | 143 | 140 |
| 3 | 98 | 90 | 85 | 80 |
| 4 | 131 | 120 | 116 | 117 |
| 5 | 127 | 117 | 114 | 107 |
| Mean | 128 ± 24 | 115 ± 21 | 111 ± 22 | 108 ± 23 |
| p Value | | 0.0032 | 0.0012 | 0.0008 |

TABLE 3

| Subject # | Initial BMI | BMI at 1 month FU | BMI at 3 month FU | BMI at 6 month FU |
| --- | --- | --- | --- | --- |
| 1 | 42 | 36 | 35 | |
| 2 | 53 | 47 | 46 | 45 |
| 3 | 34 | 31 | 30 | 28 |
| 4 | 41 | 38 | 37 | 37 |
| 5 | 41 | 38 | 38 | 34 |
| Mean | 42 ± 7 | 38 ± 6 | 37 ± 6 | 36 ± 6 |
| p Value | | 0.0033 | 0.0012 | 0.001 |

TABLE 4

| Subject # | Initial Ghrelin level (pg/ml) | Ghrelin level at 1 month FU | Ghrelin level at 3 month FU | Ghrelin level at 6 month FU |
| --- | --- | --- | --- | --- |
| 1 | 459.6 | 313.4 | 301.3 | 325.5 |
| 2 | 486.1 | 325.9 | 323.6 | 410.9 |
| 3 | 445.5 | 380.7 | 315.8 | 389.1 |
| 4 | 501.2 | 341.6 | 299.7 | 388.6 |
| 5 | 478.3 | 342.2 | 325.5 | 391.3 |
| Mean | 470.54 | 340.76 | 314.18 | 381.08 |
| p Value | | 0.0015 | 0.0002 | 0.0042 |

STATISTICAL ANALYSIS: Statistical analysis was performed using computer software (SPSS 12.0 for Windows, Lead Technologies Inc. 2003. Chicago, Ill.). All values were presented as the mean±standard deviation (±SD). Comparison of weights and plasma ghrelin levels between different time points were done with the paired t-test. A p-value of <0.05 was considered to determine statistical significance RESULTS: There were no procedural complications. Three of the five subjects described mild transient epigastric pain after the procedure. However, follow-up gastroscopies on the day after embolization and at 1-week follow-up did not reveal any abnormalities. All subjects reported a significantly decreased appetite in the first days after the procedure.

Significant progressive weight loss accompanied by reductions in plasma ghrelin levels was observed in all subjects at all follow-ups: Mean weight and BMI was reduced by 10%, 13%, and 16% at 1-, 3- and 6-month follow-up, respectively (Table 2 and 3). Mean initial weight (128.12±24.4 kg) decreased to 108±23 kg (p<0.001). Blood plasma ghrelin levels (initially 473±189) were significantly lower at 1- and 6-month follow-up (by 29% and 36% from baseline, p<0.05) and increased slightly at the 6-month follow-up compared with 3-month follow-up while remaining 18% lower from the baseline (p>0.05).

Figure 5:
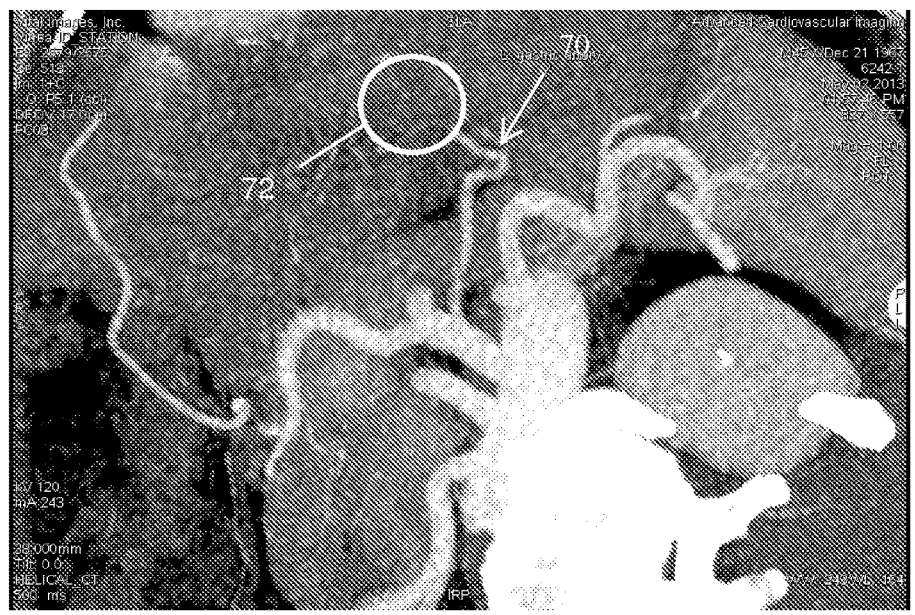
FIG. 5 depicts a CT angiography of the left gastric artery and the surrounding region three months after the distal portion of that left gastric artery was filled with microparticles.

FIG. 5 is a CT angiograph the left gastric artery 70 and the surrounding anatomy that was taken 3 months after procedure. In this figure, portions where blood is flowing are indicated in white. Because the distal portion of the left gastric artery is not visible in region 72, it is apparent that the distal portion remains occluded 3 months after procedure.

The data above demonstrates that embolization of the distal portion of the left gastric artery using microparticles is associated with significant reductions in plasma ghrelin levels and weight loss in humans. It should be noted, however, that after an initial pronounced decline in ghrelin levels after the procedure, the levels did increase at the last follow-up visit (i.e., at the 6 month visit), Although the levels were still lower than the pre-procedure baseline, a long-term study may be warranted to further investigate this increase.

The procedure described above appears to be safe. Specifically, there were no incidences of ulcer formation or injury to remote structures. This may be related to the selective injection into the left gastric artery of beads that are large enough in size as to not allow systemic or remote toxicity, yet small enough to avoid the potential problems described above. Note that with more extensive embolization of arteries other than the left gastric artery, the ulcer risk may be higher. For example, 40% of animals that underwent embolization of the left, short, and accessory gastric arteries developed gastric ulcers in a study by Paxton et al. These ulcers were located at the lesser curvature, suggesting a watershed effect. In addition, using the correct embolic materials as described herein apparently minimizes the extent and likelihood of injury to adjacent or remote tissue.

It should be noted that this example was a non-randomized single-arm feasibility, safety, and efficacy trial with all its inherent limitations. First, the absence of a control group does not allow definitive conclusions regarding efficacy. It is possible that the procedure and study participation led to a higher motivation for diet control and exercise. However, in this case, a decrease in plasma ghrelin levels should not be expected. Second, the intermediate-term follow-up (i.e., 6 months) is too short to make conclusions regarding long-term weight loss, as a rebound phenomenon with recurrent weight gain is conceivable. Third, though not observed in a study by the inventor, a risk of gastric ulcer formation may be significant but too small to have been observed in the study.

CONCLUSIONS: Percutaneous embolization of the distal portion of the left gastric artery with embolic beads as described in the study is feasible and appears to be safe. It leads to a reduction in plasma ghrelin levels and is accompanied by a significant weight loss at intermediate term follow-up. It may be a good tool to enhance weight loss in subjects with morbid obesity who cannot achieve weight loss by conventional means (diet and exercise) and an alternative to or complimentary to bariatric surgery.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of promoting weight loss by delivering particles into a human subject's left gastric artery, the left gastric artery having a proximal portion, a mid segment, and a distal portion, the method comprising the steps of:
    introducing a microcatheter into the mid segment or the distal portion of the human subject's left gastric artery; and
    delivering, via the microcatheter, a plurality of particles with sizes between 300 and 500 µm into the distal portion of the subject's left gastric artery, so that the plurality of particles cause endovascular flow reduction or interruption in the distal portion of the subject's left gastric artery but the plurality of particles do not block the proximal portion of the subject's left gastric artery.

2. The method of claim 1, wherein the step of introducing the microcatheter into the mid segment or distal portion of the subject's left gastric artery comprises the steps of:
    introducing a guiding catheter into the subject's left gastric artery, the guiding catheter having a distal end; and
    guiding the microcatheter through the guiding catheter and into the mid segment or distal portion of the subject's left gastric artery.

3. The method of claim 2, wherein the guiding catheter is a Judkins Right type catheter.

4. The method of claim 3, wherein the guiding catheter has a JR-4.0 shape code.

5. The method of claim 2, wherein the distal end of the guiding catheter has an S-shaped bend.

6. The method of claim 1, wherein the particles are spherical.

7. The method of claim 1, wherein the particles are compressible.

8. The method of claim 1, wherein the particles are made of polyvinyl alcohol.

9. The method of claim 8, wherein the particles are made of acrylamido polyvinyl alcohol.

10. The method of claim 9, wherein the particles are compressible and spherical.

11. The method of claim 1, wherein the microcatheter has a distal shaft that is 2 French in diameter.

12. The method of claim 1, wherein a pharmaceutical that helps to decrease production of ghrelin or other hormones is added to the particles.

13. The method of claim 1, wherein a genetic material that helps to decrease production of ghrelin or other hormones is added to the particles.

14. The method of claim 1, wherein cells that help to decrease production of ghrelin or other hormones are added to the particles.

* * * * *